(12) United States Patent
Khoobehi et al.

(10) Patent No.: US 6,524,330 B1
(45) Date of Patent: Feb. 25, 2003

(54) METHOD OF OCULAR TREATMENT

(76) Inventors: Bahram Khoobehi, 5024 Cleveland Pl., Metairie, LA (US) 70003; Gholam Peyman, 8654 Pontchartrain Blvd., Unit #1, New Orleans, LA (US) 70124; Robert Grinstead, 206 Hector Ave., Metairie, LA (US) 70005

( * ) Notice: Subject to any disclaimer, the term of this patent is extended or adjusted under 35 U.S.C. 154(b) by 149 days.

(21) Appl. No.: 09/698,877

(22) Filed: Oct. 27, 2000

(51) Int. Cl.⁷ .............................................. A61B 18/00

(52) U.S. Cl. .................................. 607/89; 606/4; 606/6

(58) Field of Search ........................... 606/4, 7; 607/89

(56) References Cited

U.S. PATENT DOCUMENTS

| | | | |
|---|---|---|---|
| 5,514,714 A | 5/1996 | Meruelo et al. | 514/561 |
| 5,576,013 A | 11/1996 | Williams et al. | 424/423 |
| 5,707,986 A | 1/1998 | Miller et al. | 514/185 |
| 5,952,311 A | 9/1999 | Kraus et al. | 514/44 |
| 6,001,882 A | 12/1999 | Fox et al. | 514/680 |

OTHER PUBLICATIONS

Zhenjun Diwu, *Novel Therapeutic and Diagnositc Applications of Hypocrellins and Hypericins,* Photochemistry and Photobiology (Invited Review), vol. 61: No. 6, pp. 529–539, 1995.

Diwu et al., *Photosensitization with anticancer agents 18 perylenequinonoid pigments as potential photodynamic therapeutic agents: preparation and photodynamic properties of amino–substituted hypocrellin derivatives,* Anti–Cancer Drug Design, vol. 8, 129–143, 1993.

Diwu et al., *Hypocrellins and their use in photosensitization,* Photochemistry and Photobiology, vol. 52: No. 3, 609–616, 1990.

Diwu and Lown, *Photosensitization with anticancer agents 16. The photo–oxidation of hypocrellin A. A mechanism study using 18–O labeling.,* J. Photochem. Photobiol. B: Biol., 18: pp. 145–154, 1993.

Diwu et al., *Design, synthesis and investigation of mechanisms of action of novel protein kinase C inhibitors: Perylenequinonoid pigments,* Biochemical Pharmacology, vol. 47, No. 2, pp. 373–385, 1994.

Diwu et al., *Photosensitization by anticancer agents 21: New perylene–and aminonaphthoquinones,* Free Radical Biology and Medicine, vol. 20, No. 4, 589–593, 1996.

Duran and Song, *Hypericin and its photodynamic action,* Photochemistry and Photobiology (Yearly Review), vol. 43, No. 6, pp. 677–680, 1986.

Ebermann et al., *Natural products form plants as potential drugs for the photodynamic destruction of tumor cells,* Journal of Photochemistry and Photobiology B: Biology 36, pp. 95–97, 1996.

Estey et al., *Hypocrellins as photosensitive for photodynamic therapy: a screening evaluation and pharmacokinetic study,* Cancer Chemother Pharmacol, vol. 37, 343–350, 1996.

Falk et al., *Lowest excited triplet states of hypericin and isohypericin,* J. Photochem & Photobiology, vol. 20 (1993) 133–137.

(List continued on next page.)

Primary Examiner—Edward K. Look
Assistant Examiner—Dwayne J. White
(74) Attorney, Agent, or Firm—Wood, Herron & Evans, L.L.P.

(57) ABSTRACT

A method for treating abnormal blood vessel growth and proliferation is disclosed. Members of the hypocrellin class of compounds such as hypocrellin A, hypocrellin B, and/or amino-substituted derivatives of hypocrellin B are administered and photoactivated with photodynamic therapy. The method may be used, for example, to treat ocular blood vessel proliferation as occurs with macular degeneration.

18 Claims, 1 Drawing Sheet

OTHER PUBLICATIONS

Fox et al., *Photoactivated hypericin is an anti–proliferative agent that induces a high rate of apoptotic death of normal transformed, and malignant T lymphocytes: Implications for the treatment of cutaneous lymphoproliferative and inflammatory disorders,* J. Infest. Dermatol. 111: 327–332, 1998.

Harris et al., *Hypericin inhibits cell growth and induces apoptosis in retinal pigment epithelial cells: possible involvement of protein kinase C,* Current Eye Research, 15: 225–262, 1996.

Kimura et al., *Hypericin inhibits choroidal endothelial cell proliferation and cord formation in vitro.,* Current Eye Research, 16: 967–972, 1977.

Lenci et al., *Spectroscopic and photoacoustic studies of hypericin embedded in liposomes as a photoreceptor model,* Photochemistry and Photobiology, vol. 62, No. 1, pp. 199–204, 1995.

Gerald G. Miller et al., *Uptake kinetics and intracellular localization of hypocrellin photosensitizers for photodynamic therapy: a confocal microscopy study,* Photochemistry and Photobiology, vol. 61, No. 6, 632–638, 1995.

Wang Nenghui and Zhang Zhiyi, *Relationship between photosensitive activities and chemical structure of hypocrellin A and B,* Photochemistry and Photobiology, vol. 14, 207–217, 1992.

Tahara et al., *The antidepressant hypericin inhibits progression of experimental proliferative vitreoretinopathy,* Current Eye Research, vol. 19, No. 4, pp. 323–329, 1999.

Zang et al., *EPR–spin trapping kinetic studies of superoxide radicals produced by photosensitized hypocrellin A, a photodynamic therapeutic agent,* Biochem. and Mol. Biol. International, vol. 38, No. 4, Apr. 1996.

Zang et al., *Generation of free radicals during photosensitization of hypocrellin A and their effects on cardiac membranes,* Photochemistry and Photobiology, vol. 56, No. 4, 453–462, 1992.

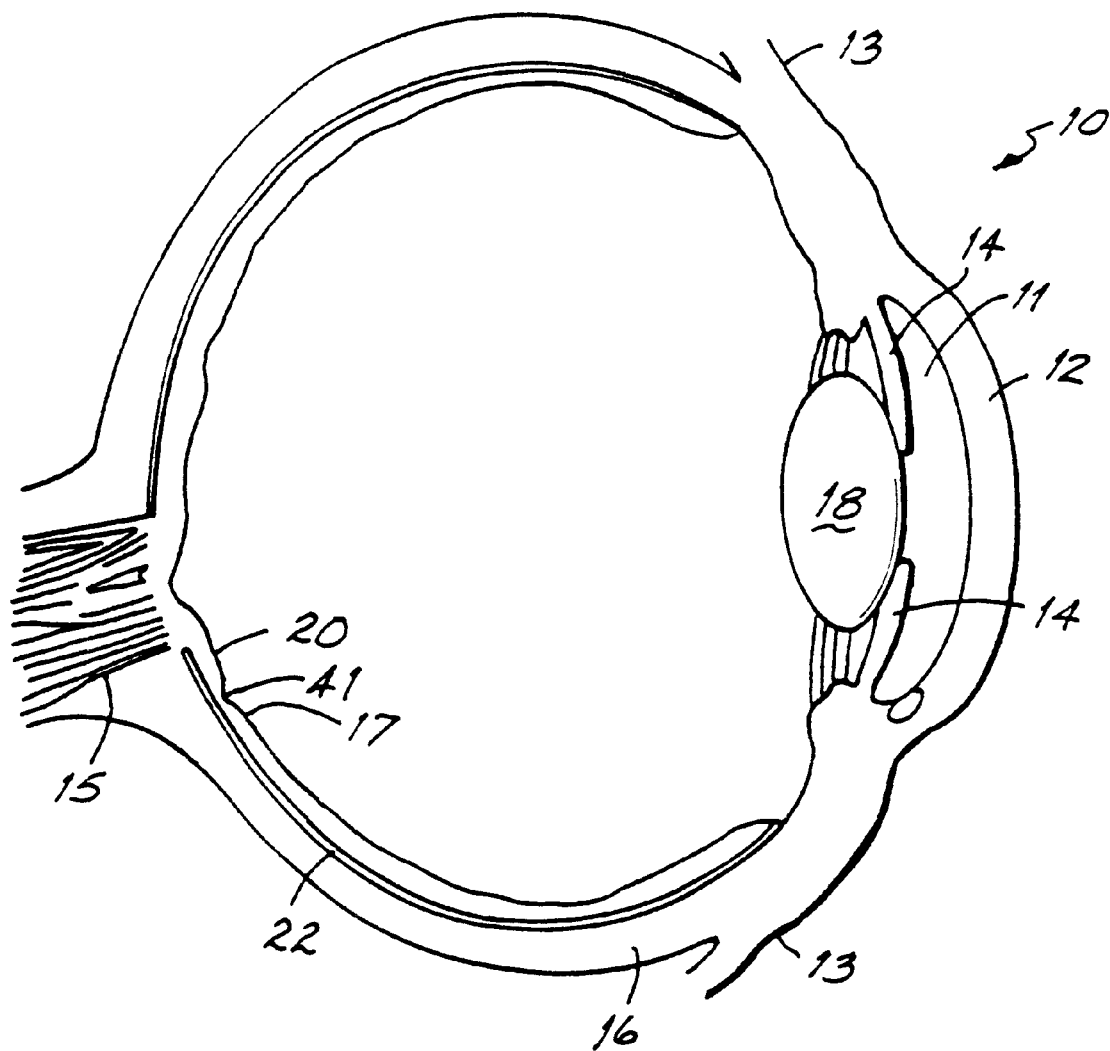

METHOD OF OCULAR TREATMENT

FIELD OF THE INVENTION

This invention relates to a composition and method to treat abnormal blood vessel proliferation in the eye.

BACKGROUND OF THE INVENTION

Many therapeutic treatments of pathological conditions involve selective targeting of specific tissues or cells for destruction. For example, a goal in cancer therapy is to destroy only malignant cells while leaving normal cells undisturbed. As another example, a goal in ophthalmology is to destroy new abnormal blood vessels in the eye that can result in visual impairment if allowed to proliferate, while leaving normal existing blood vessels intact.

In the mammalian eye, macular degeneration (also called age related macula degeneration, AMD) is a pathological condition that results in proliferation of new blood vessels in the subretinal area. The new blood vessels proliferate from the choriocapillaris through defects in Bruch's membrane beneath or on top of retinal pigment epithelium (RPE), and form vascular membranes. While the presence of the new vessels themselves is not problematic, new vessels leak blood and other serous fluid which accumulate in surrounding spaces. It is this fluid accumulation that leads to visual impairment. For example, in the retina, both the large vessels and the capillaries normally have intact vessel walls. In the choroid, the large vessels normally have intact vessel walls, but the capillary walls or membranes contain fenestrations or openings. Any endogenous or exogenous fluid present in these capillaries, for example, blood, serous fluid, solubilized drug, etc. will leak outside the vessels and into the surrounding area. The accumulation of fluid can result in serous and hemorrhagic detachment of the RPE and neurosensory retina, and can lead to loss of vision due to fibrous deform scarring. More than 90% of cases having significant loss of central vision in AMD are attributed to choroidal neovascularization and the resulting exudation and scarring. Choroidal neovascularization occurs in about 8–10% of all patients with AMD, and is also seen in patient with pathologic myopia and presumed ocular histoplasmosis syndrome, as well as other idiopathic conditions.

Simply put, control of blood vessels is a way to treat certain pathological conditions such as macular degeneration. Macular degeneration results in new, inherently "leaky", blood vessels in the eye. These new leaky vessels allow fluid to escape and pool in the surrounding tissues. The accumulation of fluid results in scar formation which can damage the eye and lead to altered vision. A goal is to destroy the new abnormal blood vessels and/or to prevent their growth.

Thus, a method to prevent or control the growth of subretinal blood vessels is needed. Such a method will in turn protect vision by protecting retinal integrity.

Summary of the Invention

The invention is directed to a therapeutic method to treat or prevent abnormal blood vessel formation and proliferation. Such an invention is useful in a variety of pathological conditions, for example, abnormal blood vessels in the eye as occurs in macular degeneration.

The method uses hypocrellin compounds. A member of the hypocrellin class of compounds is administered to reach the vessel and is photoactivated in the vessel. The hypocrellin class includes hypocrellin A, hypocrellin B, and derivatives such as amino-substituted hypocrellin B.

This invention will be further described in the following figure, detailed description and example.

BRIEF DESCRIPTION OF THE FIGURE

The Figure is a schematic cross-sectional view of a mammalian eye.

DETAILED DESCRIPTION

A method for therapy of abnormal blood vessels is disclosed. Therapy includes either prevention of new vessel growth, or prevention of further growth and/or proliferation of existing vessels. The method is applicable to any vessel that can be subjected to irradiation, either directly or through invasive means. Vessels to be treated include, but are not limited to, ocular vessels and peripheral vessels. Thus, the invention encompasses treating a condition which either is known or suspected to exist, or preventing advancement of a known or suspected condition, involving abnormal blood vessels. The method utilizes the properties of related compounds hypocrellin A, hypocrellin B, and amino-substituted derivatives of hypocrellin B to achieve this result.

One or a combination of the hypocrellins are administered and are photoactivated. The compound may be administered by a number of routes as long as an amount sufficient to achieve therapy reaches the vessel. Such routes include oral administration, intravenous injection, or intraarterial injection. The compound may be administered in a pharmaceutically acceptable form, either alone or in combination with carriers such as, but not limited to, liposomes, cyclodextrins, lipid suspensions, polymer suspension, lipophilic solvents, microcapsules, microbeads, etc.

The inventive method is useful to treat abnormal blood vessel proliferation, for example, as occurs in the eye in macular degeneration. With reference to the Figure, a mammalian eye 10 is shown. The locations of the anterior chamber 11, cornea 12, conjunctiva 13, iris 14, optic nerve 15, sclera 16, macula lutea 17, lens 18, retina 20 and choroid 22 are illustrated. Macular degeneration is a pathological, progressive age-related degeneration in the macula lutea 17 of the retina 20. The macula lutea 17 is located in the center of the posterior part of the retina 20 and is the most sensitive portion of the retina 20. In the center of the macula lutea 17 is a depression, the fovea centralis 41, from which rods are absent. About one-tenth inch inside the fovea 41 is the point of entrance of the optic nerve 15 and its central artery. At this point, the retina 20 is incomplete and forms the blind spot. In an adult with macular degeneration, there is growth of new subretinal blood vessels whose walls or membranes are altered in that they also contain fenestrations. Visual impairment results from this neovascular tissue because of fluid leakage and accumulation in surrounding spaces. Treatment of macular degeneration is therefore directed to destruction of the neovascular tissue, and/or prevention of new abnormal blood vessel growth.

Photodynamic therapy (PDT) is used to treat a variety of conditions. In PDT, an agent that is sensitive to light and activated when exposed to light of a defined wavelength (photosensitive agent) is administered to an individual for subsequent phototreatment. The photosensitizing agent, activated by the wavelength of light selected to correspond to the absorbance maximum of the particular agent, produces reactive oxygen species such as hydroxyl or oxygen free radicals which kill cells or tissues at that site. The free radicals formed in phototreatment directly injure cells by disrupting normal cellular processes and producing localized damage to endothelial cells, platelet aggregation, and endovascular thrombosis, and thus provide an additional mechanism of cellular injury or death. Since the cytotoxic effect is localized due to the short half-life of the radicals, pathological tissues or cells are selectively destroyed over normal tissues or cells. These radicals disrupt microvascular structures in the treatment area and result in subsequent tissue damage. The extent of the damage may vary, but may include death of some or all of the cells that comprise the tissue. Thus, treatment may range from cell injury to cell death.

As the process is a photochemical reaction, however, thermal damage to surrounding tissue is limited. PDT is a method that is selective for destruction of a particular cellular or tissue site. The cytotoxic species formed are locally confined to the radiation site since they have short diffusion distances. A laser may be used to target radiation to only a specific site to be treated; the low energy levels of the laser treatment in PDT spare normal adjacent tissues. Since photoactivation leads only to localized, selective photochemical thrombosis, PDT is selective for a specific area.

The time period between administration of the agent and phototreatment is between about 1–60 minutes. PDT ideally occurs when levels of the photosensitizing agent at the desired site are at a maximum.

PDT is more protective of normal tissue than other methods of phototherapy. For example, PDT is more protective than laser photocoagulation because there is no heat applied, allowing localization of the PDT to a specific area. PDT has gained wide clinical acceptance as a mechanism for producing localized, selective photochemical thrombosis. For example, PDT has been suggested as being able to play an important adjuvant role in treatment of cancers of the gastrointestinal tract and has been used to treat cancers of the esophagus, duodenum and colon.

Several photosensitive agents are known. For example, aminolevulinic acid (ALA) is an endogenous compound that forms the photosensitizing agent protoporphyrin IX in the biosynthetic pathway of heme. However, ALA is orally administered, absorbed by the gastrointestinal tract, and metabolized to the photoactive species. A drawback of this treatment is that the oral route of administration of the agent leads to a weaker photosensitizing response than other routes of administration, e.g., intravenous administration.

Thus, other agents would be desirable for PDT, particularly with ophthalmologic PDT, since these results have not been as promising. PDT has been found to be too nonspecific in that normal retinal vessels are damaged along with subretinal vessels. Also, there are unresolved issues with PDT such as the time interval between drug administration and light application, and the selective targeting of abnormal vessels with drug, light, or both. Additionally, laser treatment must continually be repeated as new vascularizations occur. For example, PDT must be performed every two to three months for about two years, which makes treatment by PDT alone both costly and inconvenient.

The hypocrellins such as hypocrellin A and hypocrellin B, and derivatives of hypocrellin A and hypocrellin B such as amino-substituted hypocrellin B, are naturally occurring, structurally related perylenequinone pigments derived from plants and fungi. The hypocrellins are members of the bioflavinoid family, are known photosensitizing agents used in PDT of human tumors, and demonstrate phototoxic, light, and oxygen dependent activities. Hypocrellin A is non-toxic in the absence of light and thus can be selectively activated by application of light. The hypocrellins may be synthesized in pure monomeric form or may be easily purified, they exhibit a low aggregation tendency, they show reduced normal tissue photosensitivity because of rapid in vivo metabolism, and they have high quantum yields of singlet oxygen. Dose escalation studies in rodents indicate that potentially photosensitizing doses promote no demonstrable systemic toxicity.

When these drugs are in circulation, laser or white light can be applied to activate those compounds in the retina, choroid, or sub-retinal membrane abnormal or pathogenic vasculature, or neovascular tissue, to close desired vessels. PDT is by application of light radiation. Exposure of light radiation is preferentially restricted to only the area to be treated, for example by use of a laser to direct only a narrow beam of light to the area. This avoids or decreases damage to normal vessels and tissues. The laser may be used at a power density as low as 600 $mW/cm^2$ and energy density (irradiance) as low as 16 $J/cm^2$.

Photoactivation of Hypocrellin A was evaluated by intravenous administration of 0.5 mg/kg Hypocrellin A under the following conditions: a laser power between 10–60 mW, an exposure time of 10–60 sec, and a laser spot size of 2 mm diameter, which correspond to an energy density of 16–95 J/cm. When the dose of Hypocrellin A was higher than 0.5 mg/kg, laser parameters were reduced. Hypocrellin A was delivered in liposomes.

Photosensitized tissues are irradiated with light at a wavelength corresponding to the absorbance spectrum of the particular photosensitizing agent. The optimal wavelength for phototreatment is selected on the basis of the appropriate action spectrum of the photosensitizing agent. For example, the radiation wavelength is in the range of about 500–650 nm when hypocrellin A is administered.

EXAMPLE

Rabbits (twenty-five Dutch belted pigmented, 2–3 kg body weight), were administered hypocrellin A (Molecular Probes, Eugene, Oreg.) by systemic injection into the ear vein. Animals were anesthetized by intramuscular injection of ketamine hydrochloride (50 mg/kg) and xylazine hydrochloride (5 mg/kg). Pupils were dilated with 2.5% phenylephrine and 0.5% tropicamide.

Hypocrellin A was incorporated into liposomes composed of phosphatidylcholine (PC), phosphatidylglycerol (PG), cholesterol, or dipalmitoyl phosphatidylcholine (DPPC), dipalmitoyl phosphatidylglycerol (DPPG) (Avanti Polar Lipids, Pelham, Ala.), with or without cholesterol, using methods known to one of skill in this art. In general, large unilamellar vesicles (LUV) were formed using the reverse phase evaporation method of Szoka and Papahadjopoulos (Proc. Natl. Acad. Sci. USA 1978; 75:4194–4198). Lipids (100 mg PC, 25 mg PG, and optionally 15 mg cholesterol) and 1 mg hypocrellin A were dissolved in chloroform. The solution was placed in a round flask under rotary evaporation (Buschi Laboratoriums-teenik AG, Flawil, Schewiz) to make a thin film. The dried material was dissolved in 6 ml chloroform and 12 ml ether.

The aqueous phase consisted of 4 ml HEPES buffered saline (145 nM NaCI, 2 mM KCI, 10 mM HEPES buffer, pH 7.4, 300 mOsm). This was added to the chloroform/ether solution, the flask was filled with nitrogen gas and subjected to ultrasound at 40° C. for two minutes to form a homogeneous emulsion, which was transferred to a rotary evaporator. At pressures below about 400 mm Hg, the emulsion began to bubble extensively as the organic phase was drawn off. The pressure was gradually decreased to about 150 mm Hg. The foaming emulsion was vented whenever it neared the top of the flask. Progressively higher vacuum was used to maintain foaming. As the process continued, the foaming decreased. At a pressure of about 100 mm Hg, foaming ceased and the procedure was completed. The process yielded large, negatively charged, unilamellar liposomes with HEPES buffer encapsulated into the aqueous phase and hypocrellin A incorporated into the bilayers of the liposomes. Before injection, the LUV were filtered through 0.8 μm pores.

The hypocrellin preparation was administered as an intravenous bolus into the marginal ear vein. The dose of hypocrellin administered was 500 μg/kg in a volume of about 2 ml. However, doses in the range of about 100–2000 pg/kg may also be administered. Control animals received vehicle (liposomes without hypocrellin A in a saline solution) only.

After administration of compound, for example, 10–15 minutes after hypocrellin A administration, PDT was initiated upon application of laser irradiation with a dye laser (Coherent, Palo Alto, Calif.). Prior to light application, a lens with a focal length of 25 cm was placed in front of the laser beam to prevent interference with the slit lamp light path and to enlarge the spot size produced by the 500 μm setting of the laser to 2 mm on the retina. A spot size of 2 mm was used throughout. A plano fundus contact lens was placed on the cornea, with methylcellulose gel as a coupler, to null the refraction of the cornea. Animals were positioned in a stereotactic support attached to the slit lamp to maintain precise alignment.

The wavelengths were tested: yellow (568 nm) and red (647 nm). Laser powers were in the range of about 10 mW to about 60 mW. Duration of irradiation was for a minimum of 10 seconds to a maximum of 60 seconds. The photodynamic effect is not only related to the irradiance, but power and duration as well. Fluence (irradiance) is the product of power and duration divided by the spot size, but with a constant spot size, irradiance is a function of power and duration only. Fluence was in the range of 3.2 to 95.5 J/cm$^2$. A fluence of 19.1 J/cm$^2$ that showed no effect when the power was 10 mW and the duration was 60 seconds, yielded a response visible on the angiogram 24 hours post PDT when the power was 60 mW and the duration was 10 seconds. In one embodiment, the lowest possible power and duration that induce the minimal fluorescein angiographic response is used.

The irradiations were done in the avascular retina, below the optic disc. All combinations of power and duration for each wavelength was repeated twice. Parallel controls were irradiated using the same parameters.

Baseline fundus photography and indirect ophthalmoscopy were performed before PDT, and no defects were found. For visualizing vessels at desired times after treatment, animals were administered 10% sodium fluorescein at a dose of 0.5 mg/kg by injection into the marginal ear vein. Angiography was performed using a scanning laser ophthalmoscope camera (Rodenstock Model 101, Ottobrunn, Riemerling, Germany).

Immediately after the second fluorescein examination, eyes were enucleated and fixed in 2% paraformaldehyde and 3% glutaraldehyde for 24 h. The areas of PDT treatment were surgically excised and specimens were dehydrated in ethanol, embedded in resin, subjected to serial sectioning and staining with 1% toluidine blue for light microscopy.

The eyes of control animals revealed no detectable funduscopic or angiographic changes in the choriocapillaris or overlying retina, regardless of the power or duration of irradiation.

The eyes of treated animals subjected to laser irradiation at 568 nm (yellow laser) showed no retinal changes in the treated area during or immediately after laser irradiation. The results of fluorescein angiography 2 and 24 hours after irradiation are shown in the following table.

| Power (mW) | Duration (sec) | Irradiance (J/cm$^2$) | Fluorescein Angiogram 2 hours post PDT | 24 hours post PDT |
|---|---|---|---|---|
| 10 | 10, 20, 30, 40, 50, 60 | 3.2–19.1 | No response | No response |
| 20 | 10, 20, 30, 40, 50, | 6.4–31.8 | No response | No response |
| 20 | 60 | 38.2 | No response | Minimal H |
| 30 | 10, 20, 30 | 9.6–28.6 | No response | No response |
| 30 | 40, 50, 60 | 38.2–57.3 | No response | H |
| 40 | 10 | 12.7 | No response | No response |
| 40 | 20, 30, 40, 50, 60 | 25.4–76.4 | No response | H |
| 50 | 10, 20, 30, 40, 50, 60 | 15.9–95.5 | No response | H |
| 60 | 10 | 19.1 | No response | H |
| 60 | 20 | 38.2 | H | H |
| 60 | 30 | 57.3 | H | H |

H = hyperfluorescence

Where a fluorescence effect was observed, choroidal vascular occlusion in the irradiated area appeared as a hypofluorescence in the early phase of the fluorescein angiogram, indicating vessel treatment. In the mid-phase, the hypofluorescence was surrounded by hyperfluorescence at the edges of the treatment area. In the late phases, the hyperfluorescence filled the entire treated area.

As noted in the table, the lower power (10 mW) produced no effect, regardless of the duration of the irradiation, at either 2 or 24 hours. With 20 mW power, durations from 10–50 seconds had no effect; a minimal response was seen at 24 hours with a 60-second irradiation (38.2 J/cm$^2$). At 30 mW power and 10–30 seconds duration, there was no response; with 40, 50, or 60 seconds duration (38.2 to 57.3 J/cm$^2$), the fluorescence effect was seen at 24 hours. With 40 mW power for 10 seconds, there was no response at either 2 or 24 hours; at the same power, 20, 30, 40, 50 and 60-second irradiations (12.7 to 76.4 J/cm$^2$) had no effect at 2 hours, but did produce the fluorescence effect at 24 hours. Similarly, at 50 mW power and 10, 20, 30, 40, 50 or 60 seconds duration (15.9 to 95.5 J/cm$^2$), there was no response at 2 hours, whereas the fluorescence effect was observed at 24 hours. Thus, none of the powers (from 10 mW to 50 mW) combined with any of the durations tested (10–60 seconds) resulted in changes in the fluorescein angiogram performed 2 hours after PDT. At 24 hours, a response was seen with low power (20 mW) and long duration (60 seconds) or higher power (30, 40, 50 mW) and shorter durations (40, 20, and 10 seconds, respectively).

At 60 mW power, irradiation for 10 seconds (19.1 J/cm$^2$) produced no response at 2 hours, followed by a fluorescence effect seen in the angiogram at 24 hours. With 20 or 30 seconds of irradiation (38.2 and 57.3 J/cm$^2$), the fluorescence effect was seen at both 2 and 24 hours after PDT, and therefore longer durations were not tested at this power.

Rabbits injected systemically with hypocrellin A at a dose of 500 mg/kg and subjected to laser irradiation at 647 nm (red laser) showed no demonstrable funduscopic or angiographic changes with any of the power levels or durations tested.

Eyes of animals that did not receive hypocrellin A were irradiated using the same parameters (controls) revealed no histologic changes. All eyes that developed angiographic changes showed occlusion of the choriocapillaris by light microscopy 24 hours after laser irradiation. No damage to inner or outer retinal layers was seen.

The results demonstrate that the effects are photochemical and that there are no associated thermally induced alterations in the retina choroid.

It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A therapeutic method of vessel treatment in a mammal comprising administering a compound selected from the group consisting of hypocrellin A, hypocrellin B, amino-substituted derivatives of hypocrellin B, and combinations thereof with a carrier to said vessel of said mammal and providing a light source to said vessel under conditions sufficient to photoactivate said compound and treat said vessel, wherein said carrier is selected from the group consisting of liposomes, cyclodextrins, lipid suspensions, polymer suspensions, lipophilic solvents, microcapsules, microbeads, and combinations thereof.

2. The method of claim 1 wherein said compound is administered by intravenous injection.

3. The method of claim 1 wherein said compound is administered orally.

4. The method of claim 1 wherein said compound is administered prior to photoactivation.

5. The method of claim 1 wherein said compound is at a dose in the range of about 100–2000 µg/kg.

6. The method of claim 1 wherein said light source is provided in the range of about 500–650 nm.

7. The method of claim 1 wherein said photoactivation is by laser.

8. The method of claim 1 wherein said vessel in an ocular vessel.

9. The method of claim 8 for the treatment of macular degeneration.

10. A method to treat macular degeneration comprising administering a hypercrillen with a carrier to an ocular vessel and thereafter photoactivating said hypocrellin under conditions sufficient to treat said vessel, wherein said carrier is selected from the group consisting of liposomes, cyclodextrins, lipid suspensions, polymer suspensions, lipophilic solvents, microcapsules, microbeads, and combinations thereof.

11. The method of claim 10 wherein said hypocrellin is administered 1–60 minutes prior to photoactivation.

12. The method of claim 10 wherein said photoactivation is by laser.

13. The method of claim 10 wherein said hypocrellin is hypocrellin A.

14. The method of claim 10 wherein said hypocrellin is administered in a liposome.

15. The method of claim 10 wherein said hypocrellin is at a dose in the range of about 100–2000 µg/kg.

16. A method to inhibit vessel proliferation in a mammal comprising administering a compound selected from the group consisting of hypocrellin A, hypocrellin B, amino-substituted derivatives of hypocrellin B, and combinations thereof with a carrier to said vessel of said mammal and providing a light source to said vessel under conditions sufficient to photbactivate said compound and inhibit proliferation, wherein said carrier is selected from the group consisting of liposomes, cyclodextrins, lipid suspensions, polymer suspensions, lipophilic solvents, microcapsules, microbeads, and combinations thereof.

17. The method of claim 16 wherein said vessel is an ocular vessel.

18. The method of claim 16 wherein said light source is a laser.

* * * * *